(12) United States Patent
Bindrich (10) Patent No.: US 11,785,965 B2
(45) Date of Patent: Oct. 17, 2023

(54) WATER-MISCIBLE PREPARATION OF A LIPOPHILIC COMPOUND

(71) Applicant: DEUTSCHES INSTITUT FÜR LEBENSMITTELTECHNIK E.V, Quakenbrueck (DE)

(72) Inventor: Ute Bindrich, Quakenbrueck (DE)

(73) Assignee: DEUTSCHES INSTITUT FÜR LEBENSMITTELTECHNIK E.V, Quakenbrueck (DE)

( * ) Notice: Subject to any disclaimer, the term of this patent is extended or adjusted under 35 U.S.C. 154(b) by 573 days.

(21) Appl. No.: 16/638,423

(22) PCT Filed: Aug. 13, 2018

(86) PCT No.: PCT/EP2018/071956
§ 371 (c)(1),
(2) Date: Feb. 11, 2020

(87) PCT Pub. No.: WO2019/034624
PCT Pub. Date: Feb. 21, 2019

(65) Prior Publication Data
US 2020/0178564 A1    Jun. 11, 2020

(30) Foreign Application Priority Data
Aug. 16, 2017  (DE) .................. 102017214305.3

(51) Int. Cl.
*A23J 3/10*  (2006.01)
*A23L 33/19*  (2016.01)
*A23L 29/10*  (2016.01)
*A23L 33/15*  (2016.01)
*A23L 5/30*   (2016.01)

(52) U.S. Cl.
CPC . *A23J 3/10* (2013.01); *A23L 5/30* (2016.08); *A23L 29/10* (2016.08); *A23L 33/15* (2016.08); *A23L 33/19* (2016.08)

(58) Field of Classification Search
CPC .. A23L 5/30; A23L 33/15; A23L 33/19; A23J 3/10
See application file for complete search history.

(56) References Cited

U.S. PATENT DOCUMENTS

2014/0154371 A1* 6/2014 Mathys .................. A23C 3/07
426/582

OTHER PUBLICATIONS

Buckow, Roman, et al. "Opportunities and Challenges in Pulsed Electric Field Processing of Dairy Products." International Dairy Journal, vol. 34, No. 2, 2014, pp. 199-212., doi:10.1016/j.idairyj.2013.09.002.

(Continued)

*Primary Examiner* — Erik Kashnikow
*Assistant Examiner* — Lela S. Davis
(74) *Attorney, Agent, or Firm* — Greer, Burns & Crain, Ltd.; Steven P. Fallon (57) ABSTRACT

The invention describes a process in which casein micelles suspended in an aqueous medium are treated with pulsed electric fields in order to produce casein micelles which contain at least one lipophilic compound as a preparation which is suspended in the aqueous medium. The preparation is characterized in that it has casein micelles and at least one lipophilic compound or consists thereof, wherein the lipophilic compound is connected to the casein micelles, preferably is encompassed by the casein micelles.

14 Claims, 5 Drawing Sheets

PEF2: spec. energy input / product inlet temperature (56) References Cited

OTHER PUBLICATIONS

Moeller, Henrike, et al. "Native Casein Micelles as Nanocarriers for β-Carotene: PH-and Temperature-Induced Opening of the Micellar Structure." International Journal of Food Science Technology, vol. 52, No. 5, 2017, pp. 1122-1130., doi:10.1111/ijfs.13387.

Sharma, Pankaj, et al. "Effect of Pulsed Electric Field Processing on the Functional Properties of Bovine Milk." Trends in Food Science & Technology, vol. 35, No. 2, 2014, pp. 87-101., doi:10.1016/j.tifs.2013.11.004.

Tavares, Guilherme M., et al. "Milk Proteins as Encapsulation Devices and Delivery Vehicles: Applications and Trends." Trends in Food Science Technology, vol. 37, No. 1, 2014, pp. 5-20., doi:10.1016/j.tifs.2014.02.008.

Iltchev,Plamen, International Search Report for Application No. PCT/EP2018/071956, dated Aug. 13, 2018.

\* cited by examiner

PEF2: spec. energy input / product inlet temperature

Fig. 4

PEF2: spec. energy input / product inlet temperature

PEF2: spec. energy input / product inlet temperature

Fig. 8

PEF2: spec. energy input / product inlet temperature

Fig. 9

WATER-MISCIBLE PREPARATION OF A LIPOPHILIC COMPOUND

The present invention relates to a preparation of at least one lipophilic compound that may e.g. be a lipophilic vitamin, provitamin, or a mixture of at least two of these, which preparation is miscible with water or hydrophilic foods. The invention therefore also relates to foods containing the preparation, and to the use of the preparation as an additive for foods and food supplements. Such foods and food supplements may be fat-reduced or fat-free, consist of a hydrophilic phase and/or be no emulsion and preferably contain no emulsifier. The invention further relates to a process for producing the preparation. The preparation has the advantage that the lipophilic compound contained therein is miscible with water or hydrophilic foods or food supplements, consists of natural ingredients, contains no added fat and no emulsifier, and is preferably low in fat, e.g. contains a maximum of 2 wt.-% fat, or is fat-free. The lipophilic compound is preferably stabilized within the preparation, e.g. against UV radiation and/or against oxidation. Accordingly, the lipophilic compound itself may be instable e.g. against UV radiation and/or oxygen and is stabilized within the preparation against UV and/or oxidation, in particular against oxygen.

STATE OF THE ART

Moeller et al., International Journal of Food Science and Technology, 52, 1122-1130 (2017) describes that native casein micelles are suitable as carrier for the inclusion of e.g. fat-soluble micro nutrients like beta-carotene. Casein micelles were loaded with beta-carotene by cooling to 2° C. in combination with a decrease of the pH value to 5.5.

Tavares et al., Trends in Food Science & Technology 37, 5-20 (2014) describes the encapsulation of lipophilic substances within structures similar to casein micelles that could be generated from caseinate by reducing the pH value, e.g. through carbonation, and by applying rennet, or by increasing the ionic concentration and decreasing the pH value, or from caseinate and tri-potassium phosphate by adding potassium-hydrogen-phosphate and calcium chloride.

Buckow et al., International Dairy Journal 34, 199-212 (2014) describes that pulsed electric fields (PEF) may be used for the preservation of milk.

Sharma et al., Trends in Food Science & Technology 35, 87-101 (2014) describes the effect of pulsed electric fields onto cow's milk, as well as the influence of this treatment onto the content of various vitamins.

OBJECT OF THE INVENTION

The object of the invention lies in providing an alternative preparation and a process for its production, which preparation is miscible with water and hydrophilic foods, in particular fat-free foods, and which contains a lipophilic compound.

DESCRIPTION OF THE INVENTION

The invention achieves the object by the features of the claims, in particular by a process in which casein micelles that are suspended in an aqueous medium are treated with a first pulsed electric field, then the obtained suspension of first casein micelles is mixed with at least one lipophilic compound, and subsequently this mixture is treated with a second pulsed electric field to produce casein micelles containing the at least one lipophilic compound as a preparation that is suspended in the aqueous medium. The preparation is characterized in that it has casein micelles and at least one lipophilic compound or consists thereof, wherein the lipophilic compound is connected to the casein micelles, preferably is encompassed by the casein micelles. The casein micelles are obtainable from milk, e.g. by microfiltration from skimmed milk, optionally rehydrated from the dried state.

The preparation contains the lipophilic compound, which may optionally be instable against UV and/or oxygen, in stabilized form. It is currently believed that the lipophilic compound is encompassed or enclosed by the casein micelles and thus is protected against UV and/or oxidation, e.g. by oxygen.

The release of the lipophilic compound from the preparation ensues by normal digestion, so that the lipophilic compound is released from the preparation after food intake.

The preparation is obtainable by a process having the following steps or consisting thereof:
- treating a suspension of casein micelles in aqueous medium with a first pulsed electric field (PEF-1) having a specific energy input from 20 to 150 kJ/kg, preferably 35 kJ/kg, of the aqueous suspension, having an electric field strength of 10 to 20 kV/cm, preferably 11.5 kV/cm, and having a pulse duration of 15 to 25 µs, preferably 15 µs, preferably at a pulse frequency of 150 to 250 Hz, wherein the aqueous suspension prior to the treatment with the first pulsed electric field preferably has a temperature of 1 to 60° C., for the production of a suspension of first casein micelles
- mixing the suspension of first casein micelles with a solution of the lipophilic compound, the solvent of which solution preferably is miscible with the aqueous medium, for the production of a mixture of the suspension of first casein micelles with the lipophilic compound, wherein preferably this mixture is mixed for e.g. 1 to 15 min,
- treating the mixture of the suspension of first casein micelles with the lipophilic compound, said mixture preferably having a temperature of 35 to 60° C., with a second pulsed electric field (PEF-2) having a specific energy input of from 40 to 61 kJ/kg of the mixture, e.g. at an electric field strength of 10 to 20 kV/cm, preferably 11.5 kV/cm, and at a pulse duration of 15 to 25 µs, preferably 15 µs, preferably at a pulse frequency of 150 to 250 Hz, for the production of casein micelles,
- optionally subsequently hot-keeping, e.g. at 55 to 65° C., preferably 60° C., e.g. for 5 to 10 min, optionally with or without movement of the mixture, to produce a suspension of the preparation with or of casein micelles containing the lipophilic compound,
- preferably without adding a emulsifier or a surfactant
- optionally separating the preparation from the aqueous phase and/or
- optionally drying the preparation to produce a dried preparation.

The treatment with the first electric field and/or the treatment with the second electric field preferably ensues in flow-through, e.g. at a flow rate of 20 to 30 L/h. The treatment with the first electric field and/or the treatment with the second electric field can each be carried out independently of one another with a constant or alternating polarity between two electrodes, preferably each with alternating polarity.

For native casein micelles that were separated, e.g. by microfiltration from milk, preferably from low-fat milk, the mixture of the suspension of the first casein micelles with the lipophilic compound is preferably temperature-controlled to 35 to 45° C. prior to treatment with the second pulsed electric field, the specific energy input of the PEF-2 preferably is 40 to 55 kJ/kg, and the subsequent hot-keeping is preferred, e.g. at 60° C. for κ to 10 min. For casein micelles that are in the medium in rehydrated form, e.g. rehydrated, previously dried or freeze-dried casein micelles, the mixture of the suspension of first casein micelles with the at least one lipophilic compound is preferably heated to a temperature of 50 to 60° C. prior to treatment with the second pulsed electric field, preferably the energy input of the PEF-2 is 51 to 61 kJ/kg, and preferably subsequently to PEF-2, a hot-keeping ensues at 60° C. for κ to 10 min.

The mixture of the suspension of first casein micelles with the lipophilic compound is preferably temperature-controlled to 50 to 60° C. prior to the treatment with the second pulsed electric field, the specific energy input of the PEF-2 is preferably 51 to 61 kJ/kg, and the subsequent hot-keeping is preferred, e.g. at 60° C. for 5 to 10 min.

The aqueous medium with the casein micelles suspended therein preferably contains the protein micelles at a protein content of 2 to 10 g/100 g suspension, preferably 3.0 g/100 g suspension, preferably a pH value of 6.2 to 6.4, preferably pH 6.3, preferably a conductivity of 0.8 to 1.5 mS/cm, more preferably of 1.2 mS/cm, and preferably a temperature of 2.5 to 3.5° C., more preferably 3.0° C.

The preparation containing or consisting of the casein micelles that contain the lipophilic compound can be admixed as an aqueous suspension or as a dried preparation into food masses that are low in fat or fat-free in that they do not contain any free fat in which the lipophilic compound alone cannot be dissolved.

The preparation has the advantage of containing the at least one lipophilic compound in a form that is miscible with aqueous food masses. The preparation preferably contains the lipophilic compound in a stable manner, so that even after admixing into a food mass said lipophilic compound remains essentially connected to the casein micelles, preferably remains enclosed within the casein micelles.

The lipophilic compound may be a fat-soluble vitamin, e.g. Vitamin A, D, E and/or K, or a provitamin, e.g. β-carotene, or a mixture of at least two thereof.

The food mass may e.g. be a milk product, e.g. milk, yogurt, kefir, curd cheese, cream cheese, cheese, buttermilk, pudding, milk-based or milk-free ice cream, or confectionery masses, e.g. chocolate, jelly mass, chewing gum mass, or sausages and vegetarian foods with low fat contents.

The drying of the preparation may ensue by freeze-drying, preferably by fluidized-bed drying, e.g. at a maximum of 80° C., more preferably at a maximum of 70 or at a maximum of 60° C.

The preparation is preferably admixed into a food mass at a temperature at which the lipophilic compound in the preparation is essentially preserved. The preparation may be used in food production in the same way as conventional casein-rich milk protein concentrates or dried casein-rich milk protein powder.

The invention is now described by way of examples with reference to the figures that show in FIG. 1 the content of lipophilic compound in a preparation with native casein micelles in dependence from process conditions and from the specific energy input of the PEF-2 (PEF2), FIG. 2 the specific surface area of the casein particles of the preparation with native casein micelles in dependence from the temperature of the mixture prior to PEF-2 and from the specific energy input of the PEF-2, FIG. 3 the surface potential of the casein particles of the preparation with native casein micelles in dependence from the temperature of the mixture prior to PEF-2 and from the specific energy input of the PEF-2, FIG. 4 the charge density of the casein particles of the preparation with native casein micelles in dependence from the temperature of the mixture prior to PEF-2 and from the specific energy input of the PEF-2, FIG. 5 the content of lipophilic compound in a preparation with rehydrated casein micelles in a preparation in dependence from process conditions of the PEF-2, FIG. 6 the content of lipophilic compound in % in the preparation with rehydrated casein micelles in a preparation in dependence from the process conditions of the PEF-2 in relation to a thermal stabilization process (comparison, heating only for 30 min at 60° C.), FIG. 7 the specific surface area of the casein particles of the preparation with rehydrated casein micelles in dependence from the temperature of the mixture prior to PEF-2 and from the specific energy input of the PEF-2, FIG. 8 the surface potential of the casein micelles of the preparation with rehydrated casein micelles in dependence from the temperature of the mixture prior to PEF-2 and from the specific energy input of the PEF-2, and in FIG. 9 the charge density of the casein particles of the preparation with rehydrated casein micelles in dependence from the temperature of the mixture prior to PEF-2 and from the specific energy input of the PEF-2.

EXAMPLE 1: PREPARATION OF NATIVE CASEIN MICELLES WITH β-CAROTENE

Native casein micelles were obtained from skimmed milk by microfiltration and adjusted to a protein concentration of the casein micelles of 3.0 g/100 g in whey, the pH was adjusted to 6.3 and the conductivity to 1.2 mS/cm by adding NaCl. This suspension was temperature-controlled to 3.0° C. and continuously subjected to first pulsed electric fields of alternating polarity at a flow rate of approx. 25 L/h in a treatment cell in which two colinear wall sections of titanium were formed as electrodes and were spaced apart by an insulator of aluminum oxide. The specific energy input was 35 kJ/kg suspension, the electric field strength was 11.5 W/cm, the pulse frequency was 200 Hz at a pulse duration of 15 ms. As an example of a lipophilic compound, β-carotene was dissolved in ethanol as a solvent at 0.1 g/L by stirring for 15 min and 30 s of ultrasound. The thus produced suspension of the first casein micelles was mixed per liter with 60 mL of an alcoholic 1.2 mg/100 g β-carotene solution for approx. 10 min. Due to the light sensitivity of β-carotene, this solution and the subsequent mixture with the first suspension of casein micelles was kept in the dark.

The thus produced mixture of the suspension of first casein micelles with the lipophilic compound was temperature-controlled to a temperature between 35 and 45° C. and subjected to second pulsed electric fields of alternating polarity. The specific energy input was varied for different aliquots. The resulting suspended preparation was subsequently kept hot at various temperatures. The specific energy input (spec. energy input) of this PEF-2, the temperature of the mixture prior to exposure (product inlet temperature) to the second pulsed electric field (PEF-2) and the temperatures and duration (+0 min, +5 min, +10 min) of the subsequent hot-keeping are shown in FIGS. 1 to 4, which show from left to right the measured values for the same samples that were each produced under the same process conditions.

The β-carotene content of the preparation was measured by photometry after dissolution of the casein micelles.

Figure 1:
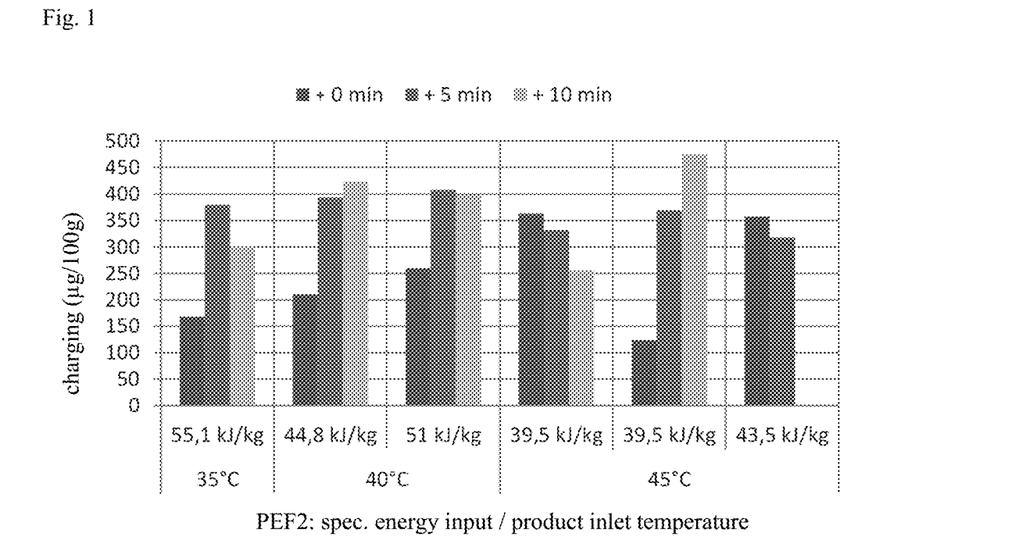

FIG. 1 shows the respectively measured contents of β-carotene at the specified values of the specific energy input used of the PEF-2, of the temperature of the mixture from the suspension of first casein micelles (product inlet temperature) prior to PEF-2 after hot-keeping for different time lengths and different temperature-controlled hot-keepings. The results show high loadings of the casein micelles with the lipophilic compound, for β-casein approx. 125 to 475 μg/100 g preparation. It becomes clear that hot-keeping for some of the combinations of specific energy input and product inlet temperature resulted in a higher loading of the casein micelles with β-carotene. An exception to the beneficial effect of hot-keeping were the sample that had a pH of 6.1 for the PEF-2 and the sample with the highest energy exposure at PEF-2, product inlet temperature 45° C. and 43.5 kJ/kg. In these samples, the highest loading of the casein micelles was already achieved by the PEF-2.

Figure 2:
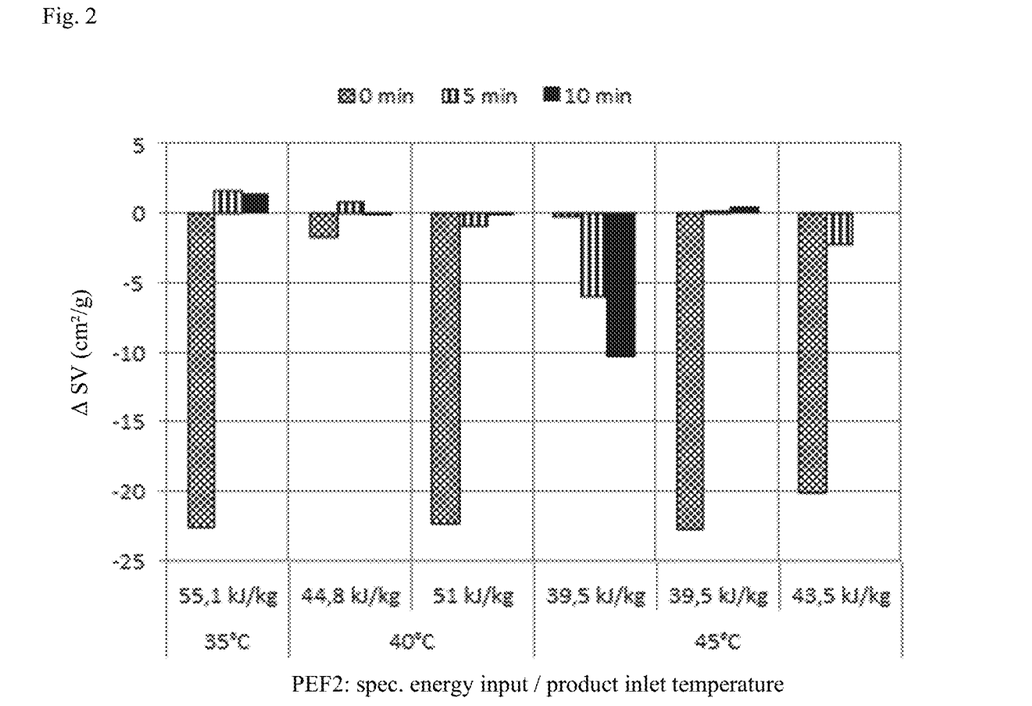

The particle surface (SV) was measured by laser diffraction spectroscopy (Malvern Mastersizer 2000) according to ISO 13320-1 and describes the disintegration of, or respectively reassociation of micelles and their agglomerates, and respectively determines the specific surface SV of the micelles over which a mass transfer can take place. The results are depicted in FIG. 2 in relation to the value measured subsequent to PEF-1 for the suspension of first casein micelles and show large changes under the specified process conditions. In general, it was shown that the specific particle surface of the preparation was reduced after the PEF-2 and, with the exception of one sample, was increased by hot-keeping subsequent to the PEF-2. This is attributed to the fact that the PEF-2 leads to an agglomeration of the casein micelles, which manifests itself in a reduction of the specific surface area. This agglomeration was resolved spontaneously, respectively without mechanical stress on the preparation by the subsequent hot-keeping, so that, with the exception of the sample at pH 6.1, essentially by the hot-keeping the specific particle surface, respectively the particle size distribution, was achieved that was had by the first casein micelles with the lipophilic compound in the suspension.

Figure 3:
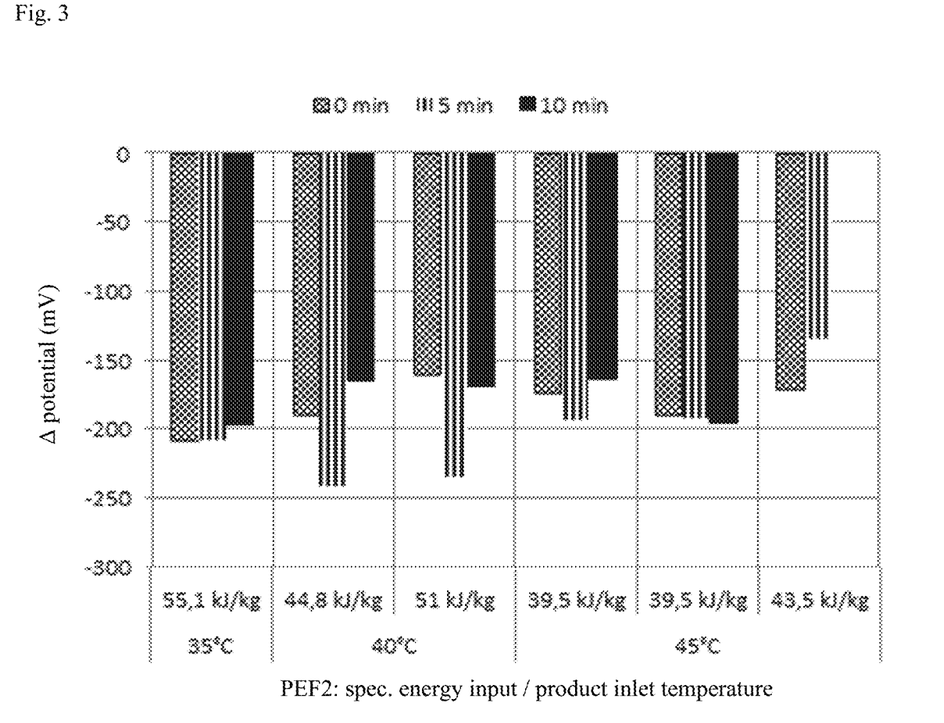

The potentials of the preparation after the PEF-2 were determined by charge measurement. The results are depicted in FIG. 3 in relation to the value measured for the suspension of first casein micelles after PEF-1 and show that the preparation after PEF-2 has strong negative potentials and also after the optional additional hot-keeping. These negative potentials are considered necessary for the stability of the preparation against agglomeration, and respectively show the stability of the preparation against agglomeration.

The surface charge and the charge density of the preparation were measured using a CAD charge measuring device (available from emtec Electronic GmbH, Leipzig). During the measurement, a suspension of the casein micelles that was mixed with 0.001 N polysodium diallyldimethylammonium chloride (Na-Poly-DADMAC) as a titration aid, was moved past a measuring cell. Through movement of the suspension, the counterions associated with the casein micelles are distorted into an uneven distribution that may be measured as positive charge for cations or as negative charge for anions or as zero charge for no charge. The measuring cell was configured to determine the charge adsorption caused by the movement. The charge density can be determined by means of the consumption of titration aid in relation to the specific surface area of the casein micelles.

Figure 4:
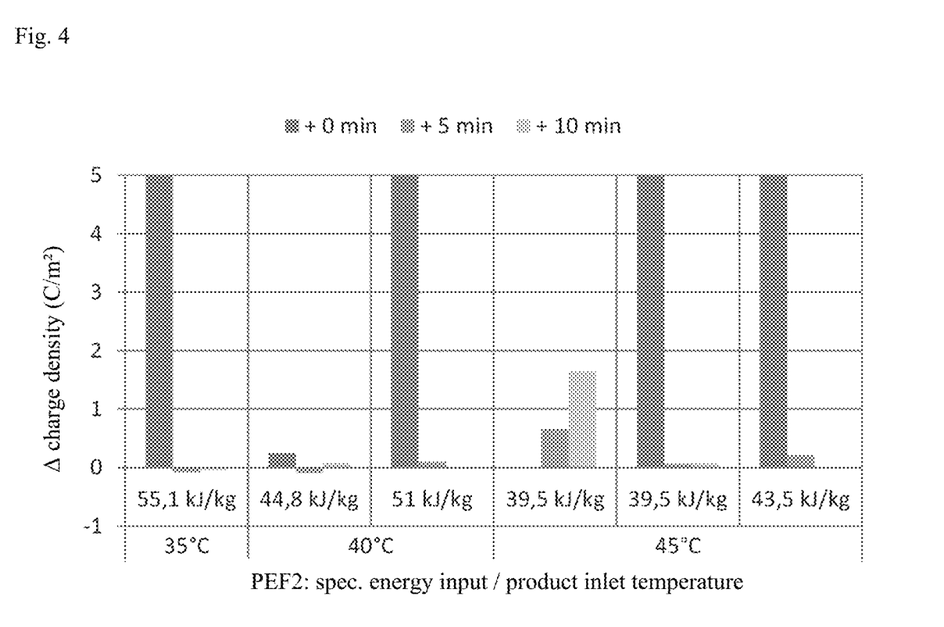

The results are depicted in FIG. 4 in relation to the value measured for the suspension of first casein micelles after PEF-1 and show that after PEF-2 the preparation has high charge densities, which are reduced by the subsequent hot-keeping, again with the exception of the preparation at pH 6.1. Since the formation of loose agglomerates is associated with a higher charge density due to the strong reduction of the particle surface, the high charge density also contributes to the dissolution of the agglomerates. Furthermore, the additional hot-keeping does not seem to cause any significant change in the charge density compared to the charge density of the suspension of first casein micelles, which was determined after PEF-1.

EXAMPLE 2: PREPARATION FROM REHYDRATED CASEIN MICELLES WITH β-CAROTENE

The process for the production of Example 1 was repeated using casein micelles (available from Sachsenmilch Ingredients) that were rehydrated in dist. water from the dry state.

The mixture of the suspension of first casein micelles with β-carotene as lipophilic compound was temperature-controlled to a temperature between 50 and 60° C. and subjected to second pulsed electric fields of alternating polarity. The specific energy input was varied for different aliquots. The resulting suspended preparation was subsequently kept hot at various temperatures. The specific energy input (spec. energy input) of this PEF-2, the temperature of the mixture prior to subjecting (product inlet temperature) to the second pulsed electric field (PEF-2) and the temperatures and duration (+0 min, +5 min, +10 min) of the subsequent hot-keeping are shown in FIGS. 5 to 9, which show, from left to right (columns in Figures), the measured values for the same samples that were each produced under the same process conditions.

Figure 5:
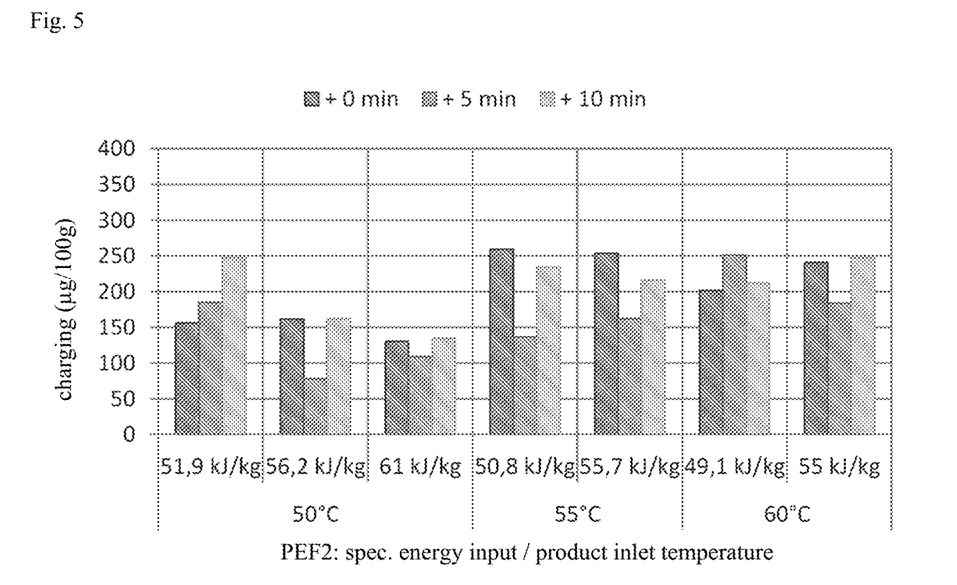
Figure 6:
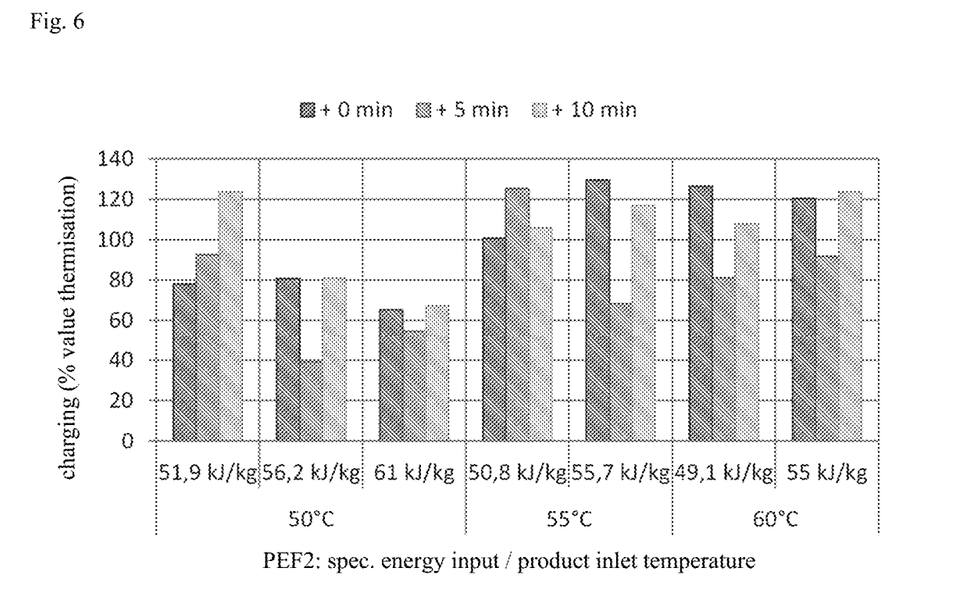

The measured values for the β-carotene content of the preparation are depicted in FIG. 5 as absolute and in FIG. 6 as % in relation to the thermal stabilization process as a comparison (heating 30 min at 60° C.). These results show that with an overall high energy supply, e.g. a product inlet temperature of 55° C. for the PEF-2, a specific energy input of 55.7 kJ/kg, as well as a product inlet temperature of 60° C. for the PEF-2 and a specific energy input of 49.1 and 55 kJ/kg, high lipophilic compound contents of the preparation are obtained, correspondingly no subsequent hot-keeping is necessary or may also reduce the content.

Figure 7:
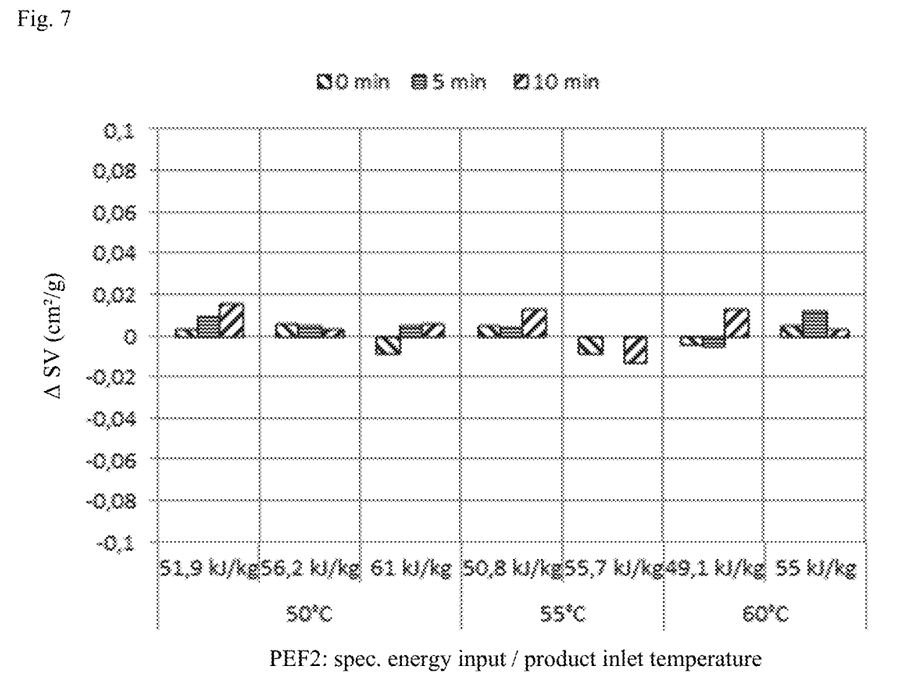

The specific surface area of the particles of the preparation, depicted in FIG. 7, may be increased or decreased by the process conditions. In this preparation, too, the increase in the specific surface area is attributed to the disintegration of aggregates of casein micelles, the reduction to the formation of aggregates.

Figure 8:
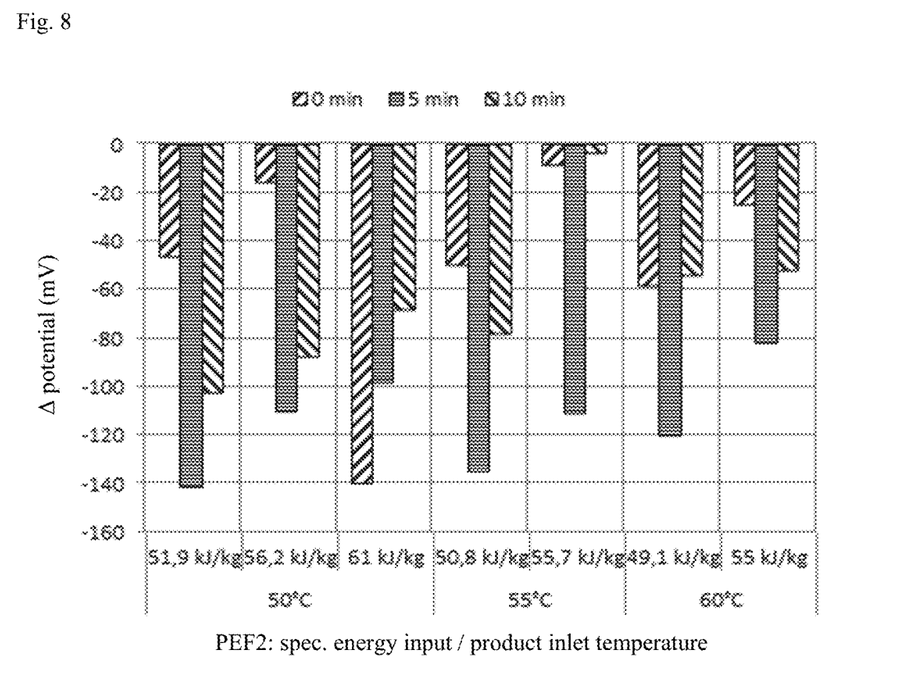

The relative surface potential of the preparations from rehydrated casein micelles is depicted in FIG. 8 in relation to the state prior to the PEF-2 treatment and shows that the surface potential results in a stronger negative surface potential from the process without or with hot-keeping subsequent to the PEF-2. This stronger negative surface potential is believed to stabilize the preparation or respectively the casein micelle particles contained therein.

Figure 9:
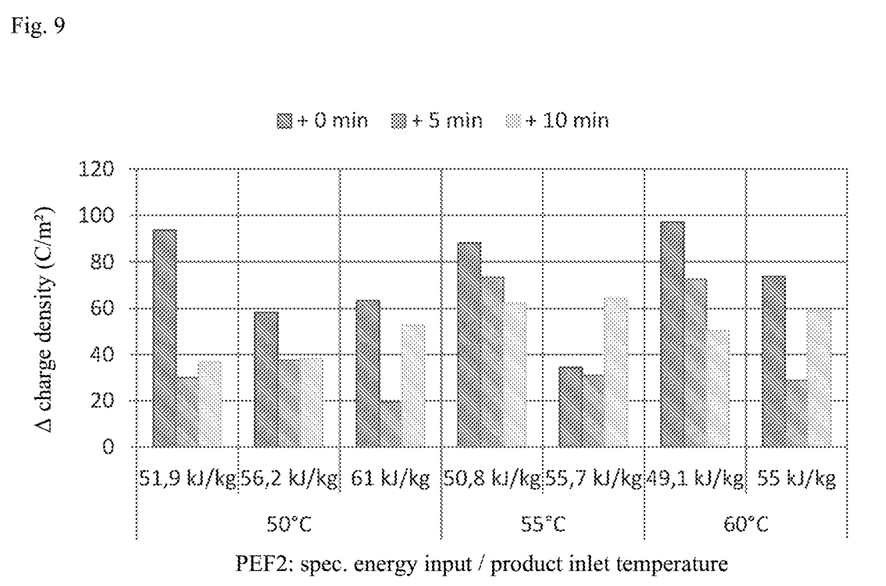

The measured values for charge densities of the preparations from rehydrated casein micelles shown in FIG. 9 show that the low specific surface areas are associated with high charge densities.

These results might also show that the PEF-2 at higher energy input leads to the irreversible formation of lumps of casein micelles.

The invention claimed is:

1. Process for producing a water-miscible preparation of at least one lipophilic compound with the steps of
    treating a suspension of casein micelles in an aqueous medium with a first pulsed electric field (PEF-1) having a specific energy input of from 20 to 150 kJ/kg of the aqueous suspension, having an electric field strength of 10 to 20 kV/cm and having a pulse duration of 15 to 25 µs, wherein the aqueous suspension has a temperature of 1 to 60° C., for the production of a suspension of first casein micelles
    mixing the suspension of first casein micelles with a solution of the lipophilic compound for the production of a mixture of the suspension of first casein micelles with the lipophilic compound,
    treating the mixture of the suspension of first casein micelles with the lipophilic compound with a second pulsed electric field (PEF-2) having a specific energy input of from 40 to 61 kJ/kg of the mixture for the production of the preparation.

2. Process according to claim 1, wherein the first pulsed electric field has a specific energy input of 35 kJ/kg of the aqueous suspension, an electric field strength of 11.5 kV/cm and a pulse duration of 15 µs.

3. Process according to claim 1, wherein the suspension of casein micelles in aqueous solution is treated with the first pulsed electric field at a pulse frequency of 150 to 250 Hz.

4. Process according to claim 1, wherein the solvent for the lipophilic compound is miscible with the aqueous medium.

5. Process according to claim 1, wherein prior to treatment with the second pulsed electric field the suspension of first casein micelles with the lipophilic compound has a temperature of 35 to 60° C.

6. Process according to claim 1, wherein the second pulsed electric field has an electric field strength of 10 to 20 kV/cm, a pulse duration of 15 to 25 µs, at a pulse frequency of 150 to 250 Hz.

7. Process according to claim 1, wherein the suspension of casein micelles in aqueous medium contains the casein micelles at a concentration of 2 to 10 g/100 g of the suspension.

8. Process according to claim 1, wherein the suspension of casein micelles in aqueous medium has a pH of 6.2 to 6.4.

9. Process according to claim 1, wherein the suspension of casein micelles in aqueous medium has a conductivity of 0.8 to 1.5 mS/cm.

10. Process according to claim 1, wherein prior to treatment with the first pulsed electric field the suspension of casein micelles in aqueous medium is temperature-controlled to a temperature of 2.5 to 3.5° C.

11. Process according to claim 1, comprising hot-keeping the mixture of the suspension at 55 to 65° C. for up to 20 min subsequent to the treatment with the second pulsed electric field.

12. Process according to claim 1, wherein the preparation is separated from the liquid phase.

13. Process according to claim 1, wherein the preparation is dried.

14. Process according to claim 1, wherein no fat and no emulsifier or surfactant is added.

* * * * *